United States Patent [19]

Conrow et al.

[11] 4,172,089

[45] Oct. 23, 1979

[54] SUBSTITUTED AROMATIC NAPHTHALENE SULFONAMIDES

[75] Inventors: Ransom B. Conrow, Pearl River; Seymour Bernstein, New City, both of N.Y.

[73] Assignee: American Cyanamid Company, Stamford, Conn.

[21] Appl. No.: 925,595

[22] Filed: Jul. 17, 1978

Related U.S. Application Data

[62] Division of Ser. No. 782,210, Mar. 28, 1977, Pat. No. 4,117,003.

[51] Int. Cl.$^2$ ............................................ C07C 137/00
[52] U.S. Cl. .................................................. 260/456 A
[58] Field of Search .................................... 260/456 A

[56] References Cited

U.S. PATENT DOCUMENTS 4,001,204  1/1977  Krutak ............................. 260/456 A

*Primary Examiner*—A. Siegel
*Attorney, Agent, or Firm*—Claude J. Caroli

[57] ABSTRACT

Substituted benzenesulfonic acid salts and amides of naphthalenetrisulfonamides and salts thereof useful as complement inhibitors, as well as triphenyl and hexaphenyl esters of substituted benzenesulfonic acid-naphthalenetrisulfonanilides which are new intermediates for the preparation of the active naphthalenetrisulfonamides and the process for their preparation.

2 Claims, No Drawings

SUBSTITUTED AROMATIC NAPHTHALENE SULFONAMIDES

This is a division of application Ser. No. 782,210 filed Mar. 28, 1977 now U.S. Pat. No. 4,117,003.

DESCRIPTION OF THE INVENTION

This invention is concerned with novel compounds of the formula:

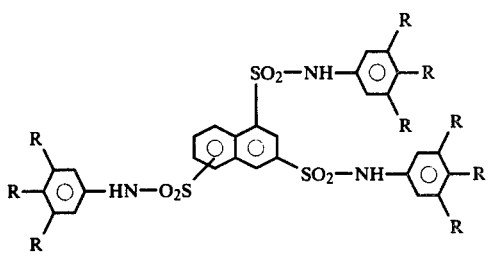

wherein R is selected from the group consisting of hydrogen and —$SO_3A$, wherein A is selected from the group consisting of alkali metal; with the proviso that each phenyl must contain at least one —$SO_3A$, and that no phenyl may contain three —$SO_3A$; and the non-toxic pharmaceutically acceptable salts thereof.

A first prefered embodiment consists of these compounds wherein R on each phenyl is at the carbon 3- and 5-positions and is selected from the group consisting of —$SO_3A$, wherein A is as previously defined.

A second prefered embodiment consists of these compounds wherein only one R on each phenyl is selected from the group consisting of —$SO_3A$, wherein A is as previously defined.

A most prefered embodiment of the first prefered embodiment consists of those compounds wherein the floating phenyl is at the carbon 6-position on the naphthalene.

A most prefered embodiment of the second prefered embodiment consists of those compounds wherein R is at the carbon 4-position.

This invention is also concerned with the following two novel intermediate compounds: 5,5′,5″-[1,3,6-naphthalenetris≡(sulfonylimino)]tris-1,3-benzenedisulfonic acid hexaphenyl ester and 4,4′,4″-[1,3,6-naphthalenetriyltris≡(sulfonylimino)]tris-benzenesulfonic acid triphenyl ester.

The novel triphenyl ester intermediate compound of the invention is prepared by reacting p-nitrobenzenesulfonic acid in pyridine with phenol at elevated temperature for one hour. The nitro-benzenesulfonic acid phenyl ester is precipitated from 10% aqueous sodium carbonate and recrystallized from ethanol. Hydrogenation with 10% palladium on carbon catalyst for 5 hours provides the amino phenyl ester which is recrystallized from benzene. The amine in pyridine is heated with 1,3,6-naphthalenetrisulfonyl chloride. The oil separated from the cold water is extracted into methylene chloride, washed with 0.5 N hydrochloric acid and water and dried. The oil dissolved in benzene:acetone (7:3) is filtered through magnesol and dried in vacuo to yield the triphenyl ester.

Additionally, the hexaphenyl ester intermediate compound of the invention is prepared by treating 1,3-benzenedisulfonic acid disodium salt with concentrated sulfuric acid at 80° C. then adding fuming nitric acid and heating at 85°–89° C. for four hours. The cooled mixture is added to ice-water, neutralized to pH 5–6 with calcium hydroxide and filtered. The aqueous mixture is adjusted to pH 10 with sodium carbonate and filtered. Evaporation of the filtrate produces a residue which is recrystallized from boiling water to give 5-nitrobenzene-1,3-disulfonic acid disodium salt. This material is refluxed 16 hours with thionyl chloride and dimethylformamide and filtered. The filtrate is concentrated to an oil which is crystallized from chloroform:carbon tetrachloride to give the disulfonyl chloride which is reacted with phenol in pyridine at elevated temperature for one hour. Addition of the cooled mixture to 10% aqueous sodium carbonate solution produces a product which is crystallized from ethanol to yield the nitro-diphenyl ester. Hydrogenation of the ester in ethyl acetate with 10% palladium on carbon catalyst for 6.5 hours yields an oil which is crystallized from benzene to give the amino-diphenyl ester. The amine in pyridine is heated with 1,3,6-naphthalenetrisulfony chloride. The mixture is poured into water and extracted with methylene chloride. The extract, after washing with dilute acid, is evaporated to a glass which is purified by column chromatography to yield the hexaphenyl ester intermediate compound of the invention. Treatment of the novel intermediate triphenyl and hexaphenyl esters with alkali metal ethoxide in dimethylsulfoxide at elevated temperature followed by acidification with acetic acid and precipitation with absolute ethanol provides the active complement inhibiting trialkali metal and hexaalkali metal salts of the invention.

In addition, treatment of 5-nitro-1,3-benzenedisulfonyl chloride with ammonium carbonate in tetrahydrofuran and crystallization of the product from ethanol-water gives the nitrodisulfonamide. Hydrogenation of the product with 10% palladium on carbon catalyst in dimethylformamide and crystallization from ethanol:ether, then water, provides the amino-disulfonamide which is reacted with 1,3,6-naphthelenetrisulfonyl chloride in pyridine at elevated temperature. The product is isolated by concentrating the mixture, dissolving the residue in water and acidifying with hydrochloric acid. The product is dissolved in dilute sodium carbonate solution and reprecipitated with hydrochloric acid to yield the hexasulfamoyl-naphthalenetrisulfonanilide.

Treatment of the above compound with alkali metal hydroxide in aqueous solution yields the trialkali metal salt from ethanol:ether (1:1).

The term "complement" refers to a complex group of proteins in body fluids that, working together with antibodies or other factors, play an important role as mediators of immune, allergic, immunochemical and/or immunopathological reactions. The reactions in which complement participates take place in blood serum or in other body fluids, and hence are considered to be humoral reactions.

With regard to human blood, there are at present more than 11 proteins in the complement system. These complement proteins are designated by the letter C and by number: C1, C2, C3 and so on up to C9. The complement protein Cl is actually an assembly of subunits designated Clq, Clr and Cls. The numbers assigned to the complement proteins reflect the sequence in which they become active, with the exception of complement protein C4, which reacts after Cl and before C2. The numerical assignments for the proteins in the complement system were made before the reaction sequence was fully understood. A more detailed discussion of the complement system and its role in body processes can be found in, for example, Bull. World Health Org., 39, 935–938 (1968); Ann. Rev. Medicine, 19, 1–24 (1968); The John Hopkins Med. J., 128, 57–74 (1971); Harvey Lectures, 66, 75–104 (1972); The New England Journal of Medicine, 287, 452–454; 489–495; 545–549; 592–596; 642–646 (1972); Scientific American, 229, (No. 5), 54–66 (1973); Federation Proceedings, 32, 134–137 (1973); Medical World News, Oct. 11, 1974, pp. 53–58; 64–66; J. Allergy Clin. Immunol., 53, 298–302 (1974); Cold Spring Harbor Conf. Cell Proliferation 2/Proteases Biol. Control/229–241 (1975); Annals of Internal Medicine, 84, 580–593 (1976); "Complement: Mechanisms and Functions", Prentice-Hall, Englewood Cliffs, N.J. (1976).

The complement system can be considered to consist of three sub-systems: (1) a recognition unit (Clq) which enables it to combine with antibody molecules that have detected a foreign invader; (2) an activation unit (Clr, Cls, C2, C4, C3) which prepares a site on the neighboring membrane; and (3) and attack unit (C5, C6, C7, C8, and C9) which creates a "hole" in the membrane. The membrane attack unit is non-specific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to the host's cells. Immunity is therefore a double-edged sword.

Activation of the complement system also accelerates blood clotting. This action comes about by way of the complement-mediated release of a clotting factor from platelets. The biologically active complement fragments and complexes can become involved in reactions that damage the host's cells, and these pathogenic reactions can result in the development of immune-complex diseases. For example, in some forms of nephritis, complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection it also results in inflammation and tissue damage in the immunopathological process. The nature of certain of the complement proteins, suggestions regarding the mode of complement binding to biological membranes and the manner in which complement effects membrane damage are discussed in Annual Review in Biochemistry, 38, 389 (1969).

A variety of substances have been disclosed as inhibiting the complement system, i.e., as complement inhibitors. For example, the compounds 3,3'-ureylenebis-[6-(2-amino-8-hydroxy-6-sulfo-1-naphthylazo)]benzenesulfonic acid, tetrasodium salt (chlorazol fast pink), heparin and a sulphated dextran have been reported to have an anticomplementary effect, British Journal of Experimental Pathology, 33, 327–339 (1952). The compound 8-(3-benzamido-4-methylbenzamido)naphthalene-1,3,5-trisulfonic acid (Suramin) is described as a competitive inhibitor of the complement system, Clin. Exp. Immunol., 10, 127–138 (1972). German Patent No. 2,254,893 or South African Patent No. 727,923 discloses certain 1-(diphenylmethyl)-4-(3-phenylallyl)piperazines useful as complement inhibitors. Other chemical compounds having complement inhibiting activity are disclosed in, for example, Journal of Medicinal Chemistry, 12, 415–419; 902–905; 1049–1052; 1053–1056 (1969); Canadian Journal of Biochemistry, 47, 547–552 (1969); The Journal of Immunology, 93, 629–640 (1964); The Journal of Immunology, 104, 279–288 (1970); The Journal of Immunology, 106, 241–245 (1971); and The Journal of Immunology, 111, 1061–1066 (1973).

It has been reported that the known complement inhibitors epsilon-aminocaproic acid, Suramin and tranexamic acid all have been used with success in the treatment of hereditary angioneurotic edema, a disease state resulting from an inherited deficiency or lack of function of the serum inhibitor of the activated first component of complement (Cl inhibitor), The New England Journal of Medicine, 286, 808–812 (1972).

The compounds of the present invention may be administered internally, e.g., orally, intra-articularly or parenterally, e.g., intra-articular, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for intravenous or subcutaneous use from about 5 to about 50 mg/kg/day, or every six hours for more rapidly excreted salts, may be used. For intra-articular use for large joints such as the knee, from about 2 to about 20 mg/joint per week may be used, with proportionally smaller doses for smaller joints. The dosage range is to be adjusted to provide optimum therapeutic response in the warm-blooded animal being treated. In general, the amount of compound administered can vary over a wide range to provide from about 5 mg/kg to about 100 mg/kg of body weight of animal per day. The usual daily dosage for a 70 kg subject may vary from about 350 mg to about 3.5 g. Unit doses of the acid or salt can contain from about 0.5 mg to about 500 mg.

While in general the sodium salts of the acids of the invention are suitable for parenteral use, other salts may also be prepared, such as those of primary amines, e.g., ethylamine; secondary amines, e.g., diethylamine or diethanol amine; tertiary amines, e.g., pyridine or triethylamine or 2-dimethylaminomethyl-dibenzofuran; aliphatic diamines, e.g., decamethylenediamine; and aromatic diamines, can be prepared. Some of these are soluble in water, others are soluble in saline solution, and still others are insoluble and can be used for purposes of preparing suspensions for injection. Furthermore as well as the sodium salt, those of the alkali metals, such as potassium and lithium; of ammonia; and of the alkaline earth metals, such as calcium or magnesium, may be employed. It will be apparent, therefore, that these salts embrace, in general derivatives of salt-forming cations.

In therapeutic use, the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as non-toxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate non-toxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form, as described herein, refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement inhibiting activity of the compounds of this invention has been demonstrated by one or more of the following identified tests:

(i) Test, Code 026 (C1 inhibitor)—This test measures the ability of activated human C1 to destroy fluid phase human C2 in the presence of C4 and appropriate dilutions of the test compound. An active inhibitor protects C2 from C1 and C4;

(ii) Test, Code 035 (C3-C9 inhibitor)—This test determines the ability of the late components of human complement (C3-C9) to lyse EAC 142 in the presence of appropriate dilutions of the test compound. An active inhibitor protects EAC 142 from lysis by human C3-C9;

(iii) Test, Code 036 (C-Shunt inhibitor)—In this test human erythrocytes rendered fragile are lysed in autologous serum via the shunt pathway activated by cobra venom factor in the presence of appropriate dilutions of the test compound. Inhibition of the shunt pathway results in failure of lysis;

(iv) Forssman Vasculitis Test—Here, the well known complement dependent lesion, Forssman vasculitis, is produced in guinea pigs by intradermal injection of rabbit anti-Forssman antiserum. The lesion is measured in terms of diameter, edema and hemorrhage and the extent to which a combined index of these is inhibited by prior intraperitoneal injection of the test compound at 200 mg/kg is then reported, unless otherwise stated;

(v) Forssman Shock Test—Lethal shock is produced in guinea pigs by an i.v. injection of anti-Forssman antiserum and the harmonic mean death time of treated guinea pigs is compared with that of simultaneous controls;

(vi) Complement Level Reduction Test—In this test, the above dosed guinea pigs, or others, are bled for serum and the complement level is determined in undiluted serum by the capillary tube method of U.S. Pat. No. 3,876,376 and compared to undosed control guinea pigs; and (vii) Cap 50 Test—Here, appropriate amounts of the test compound are added to a pool of guinea pig serum in vitro, after which the undiluted serum capillary tube assay referred to above is run. The concentration of compound inhibiting 50% is reported.

With reference to Table I, guinea pigs weighing about 300 g were dosed intravenously (i.v.) or intraperitoneally (i.p.) with 200 mg/kg of the test compound dissolved in saline and adjusted to pH 7–8. One hour after dosing, the guinea pigs were decapitated, blood was collected and the serum separated. The serum was tested for whole complement using the capillary tube assay. Percent inhibition was calculated by comparison with simultaneous controls. The results appear in Table I together with results of tests, code 026, 035, 036, Cap 50, % inhibition and Forssman shock. Table I shows that the compounds of the invention possess highly significant in vitro and in vivo, complement inhibiting activity in warm-blooded animals.

| | Biological Activities | | | | In Vivo Activity (Guinea Pig) % Inhibition | | |
|---|---|---|---|---|---|---|---|
| | | | | | Intraperitoneal Time (Minutes) | | |
| Compound | Cl 026* Wells | C-Late 035* Wells | Shunt Inhibition 036* Wells | Cap 50* | 30 | 60 | 120 |
| 5,5',5''-[1,3,6-Naphthalenetris(sulfonylimino)]tris-1,3-benzenedisulfonic acid hexasodium salt | +8** +9 | N N | +4** +2 | 21 | −85 | −86 | −86 |
| 4,4',4''-[1,3,6-Naphthalenetris(sulfonylimino)]tris-benzenesulfonic acid trisodium salt | +4 | N | N | | | | |

*Code designation for tests employed as referred herein.
**Activity in wells a serial dilution assay. Higher well number indicates higher activity. The serial dilutions are two-fold.
N = Negative

EXAMPLE 1

1,3,6-Naphthalenetrisulfonyl chloride

A mixture of 45 g of 1,3,6-naphthalenetrisulfonic acid trisodium salt, 250 ml of thionyl chloride and 5 drops of dimethylformamide is refluxed overnight. The solid remaining is filtered off and the filtrate is evaporated to dryness in vacuo. The filtrate residue is triturated with chloroform and filtered. The material is washed with chloroform and dried to give 21.0 g of the product of the example as a white solid, mp 195°–197° C.

EXAMPLE 2

5,5',5''-[1,3,6-Naphthalenetris(sulfonylimino)]tris-1,3-benzenedisulfonic acid hexaphenyl ester A 300 g amount of 1,3-benzenedisulfonic acid disodium salt is added to 400 ml of concentrated sulfuric acid in a 2 liter-three neck flask fitted with a stirrer, thermometer, condenser and a dropping funnel. The mixture is warmed to 80° C., then, without heating, 200 ml of fuming nitric acid is added dropwise maintaining the reaction temperature at 85°–89° C. When the acid addition is complete the reaction mixture is heated at 85°–88° C. for an additional 4 hours then is allowed to cool overnight. The mixture is poured slowly into ice-water and neutralized to pH 5–6 with calcium hydroxide. The precipitate formed is filtered off and the filtrate is basified to pH 10 with sodium carbonate. Again the precipitate formed is filtered off and the filtrate is concentrated to a small volume. The resulting residue is dissolved in boiling water and filtered. A total of 82 g of 5-nitrobenzene-1,3-disulfonic acid disodium salt is obtained by cooling the filtrate and collecting the precipitate.

A mixture of 45.0 g of the above material, 250 ml of thionyl chloride and 4.0 ml of dimethylformamide is refluxed for 16 hours. The solid is filtered off and the filtrate is concentrated to an oil. The oil is dissolved in chloroform, some carbon tetrachloride is added and, after standing at room temperature and cooling, a white solid is collected. The solid is washed with a small amount of chloroform and dried in vacuo to give 5-nitro-1,3-benzenedisulfonyl chloride.

To a stirred solution of 37.6 g of phenol in 200 ml of pyridine (dried over molecular sieves) at room temperature is added 32.0 g of the preceding compound (prepared in the manner described above). The mixture is heated on a steam bath for one hour, cooled to room temperature and poured into 500 ml of 10% aqueous sodium carbonate solution with vigorous stirring. The crystallized product is collected, washed with water and air dried, then is dissolved in 200 ml of methylene chloride. The solution is dried over sodium sulfate, then is concentrated by boiling. A 400 ml volume of ethanol is added portionwise to the boiling solution until all of the methylene chloride is removed. The solution is allowed to crystallize at room temperature overnight to give 38.9 g of 5-nitro-m-benzenedisulfonic acid diphenyl ester.

A mixture of 34.8 g of the compound above in ethyl acetate is hydrogenated in the presence of 10% palladium on carbon catalyst at room temperature. The mixture is filtered and the filtrate is concentrated to an oil which is crystallized from benzene. The product is collected, washed with benzene and ether, then is recrystallized twice more from boiling benzene and is dried to give 10.15 g of 5-amino-m-benzenedisulfonic acid diphenyl ester. To a solution of 9.0 g of this material in 35 ml of pyridine is added 3.28 g of 1,3,6-naphthalenetrisulfonyl chloride. The solution is heated on a steam bath for 40 minutes, cooled to room temperature and poured into 250 ml of water. The mixture is extracted with methylene chloride and this solution is washed with two 50 ml portions of 0.5 N hydrochloric acid and two 75 ml portions of water. The solution is dried over sodium sulfate, treated with activated charcoal and filtered. The filtrate is evaporated in vacuo to give a glass. The product is recovered by conventional chromatographic techniques and is dried to give 6.85 g of a pale yellow glass as the product of the example.

EXAMPLE 3

5,5',5''-[1,3,6-Naphthalenetris(sulfonylimino)]tris-1,3,-benzenedisulfonic acid hexasodium salt A solution of 1.6 g of sodium metal in 75 ml of ethanol (dried over 4 A molecular sieves) is evaporated to dryness and the product is dissolved in 75 ml of dimethylsulfoxide (dried over 4 A molecular sieves). To the solution is added 6.0 g of the product of Example 2 and the solution is heated on a steam bath for one hour. The solution is cooled to room temperature, acidified with 4.0 ml of glacial acetic acid and poured into 750 ml of absolute ethyl alcohol. The mixture is warmed, 5.0 g of sodium acetate trihydrate is added and the mixture is stirred, cooled and filtered. The product is washed with ethanol and ether, then is dissolved in 30 ml of water, filtered and poured into 350 ml of absolute ethanol to give a suspension. A 3.0 g portion of sodium acetate trihydrate is added and the mixture is filtered, washed with ethanol and ether and dried to give 4.75 g of the product of the example as a pale yellow powder.

EXAMPLE 4

4,4′,4″-[1,3,6-Naphthalenetriyltris(sulfonylimino)]tribenzenesulfonic acid triphenyl ester A 19.4 g amount of p-nitrobenzenesulfonyl chloride is added to 16.5 g of phenol in 80 ml of pyridine. The mixture is heated on a steam bath for one hour then is filtered and cooled to room temperature. The resulting yellow solution is poured into 300 ml of 10% aqueous sodium carbonate solution and stirred vigorously until the product is crystallized out. The solid is filtered, washed with water and dried, then is recrystallized from 300 ml of hot ethanol to give 20.0 g of 4-nitro-benzenesulfonic acid phenyl ester.

A mixture of 19.0 g of the preceding compound, 50 ml of dimethylformamide and 2.0 g of 10% palladium on carbon catalyst is hydrogenated on a Parr shaker for 5 hours at room temperature. The mixture is filtered and the filtrate is poured into 500 ml of water with precipitation of a solid. The mixture is stirred at room temperature for one hour, then is filtered, washed with water and dried. The solid is recrystallized from 210 ml of benzene to give 12.2 g of p-amino-benzenesulfonic acid phenyl ester.

To a solution of 11.2 g of the above amine in 50 ml of pyridine is added 6.35 g of 1,3,6,-naphthalenetrisulfonyl chloride. The resulting solution is heated on a steam bath for one hour, cooled to room temperature and poured into cold water with separation of an oil. The mixture is extracted with methylene chloride. The methylene chloride extract is washed with 0.5 N hydrochloric acid, then with water and dried over magnesium sulfate. The solvent is removed and the resulting oil is dissolved in benzene:acetone (7:3) and passed through a bed of magnesol on a sintered glass funnel. The cake is washed with additional benzene:acetone (7:3). The filtrate and washings are combined and evaporated and dried in vacuo to yield 11.9 g of the product of the example as a cream colored solid.

EXAMPLE 5

4,4′,4″-[1,3,6-Naphthalenetris(sulfonylimino)]tris-benzenesulfonic acid trisodium salt A 2.64 g portion of sodium metal is dissolved in 250 ml of ethanol. The solution is evaporated and to the the product is added 75.0 ml of dimethylsulfoxide. The mixture is swirled until near solution, then 8.8 g of the product of Example 4 is added and the solution is heated on a steam bath for one hour. The solution is cooled at room temperature, acidified with 8.0 ml of glacial acetic acid and poured into 1.2 liters of absolute ethanol. The mixture is warmed and 6.5 g of sodium acetate trihydrate is added with stirring. The mixture is cooled and the resulting beige solid is collected and washed with ethanol and ether and dried. The above solid is dissolved in 40 ml of water and filtered. The filtrate is diluted with 350 ml of ethanol and 3.0 g of sodium acetate trihydrate is added. The solid formed is filtered, washed with ethanol and ether and dried to give 6.3 g of the product of the example as a yellow solid.

EXAMPLE 6

3′,3″,3‴,5′,5″,5‴-Hexasulfamoyl-1,3,6-naphthalenetrisulfonanilide

A mixture of 37.0 g of 5-nitro-1,3-benzenedisulfonyl chloride (prepared as in Example 2), 258 ml of tetrahydrofuran (freshly distilled over lithium aluminum hydride) and 37.0 g of powdered ammonium carbonate is stirred and refluxed for 45 minutes. The mixture is filtered and the filtrate is evaporated to an oil which is solidified on mixing with water and the product is recrystallized from 325 ml of 50% aqueous ethanol by allowing to stand at room temperature, then 16 hours in an ice box. The product is collected by filtration and dried to give 25.0 g of 5-nitro-1,3-benzenedisulfonamide.

A 10.0 g portion of the preceding product, 150 ml of dimethylformamide (dried over molecular sieves) and 2.0 g of 10% palladium on carbon catalyst is hydrogenated in a Parr shaker for one hour at room temperature. The resulting mixture is filtered through diatomaceous earth and evaporated to an oil in vacuo. The product is crystallized from ethanol and ether, then is dissolved in 50 ml of methanol and filtered through diatomaceous earth. The filtrate is evaporated to dryness to give off-white crystals. This material is crystallized from 50 ml of water and dried by conventional means to give 8.0 g of 5-amino-1,3-benzenedisulfonamide.

To a solution of 6.86 g of the above product in 50 ml of pyridine is added 3.66 g of 1,3,6-naphthalenetrisulfonyl chloride (prepared as in Example 1). The resulting solution is heated on a steam bath for 30 minutes, then is concentrated in vacuo to a glass. This material is dissolved in 75 ml of hot water, filtered and acidified to pH 2 with 10 ml of concentrated hydrochloric acid. The product is separated out and solidifies by stirring and cooling. The product is collected and washed with water until neutral, then is dried in vacuo to give an off-white granular solid. The solid is dissolved in 50 ml of methanol and the solution is diluted with 100 ml of water. The precipitate formed is filtered, then is dissolved in 16.0 ml of 1 M aqueous sodium carbonate solution plus 30 ml of water. The solution is filtered and acidified to pH 2 with 3.0 ml of concentrated hydrochloric acid to give a colorless precipitate. The mixture is filtered and the precipitate is washed with water, ground up and dried by conventional means to yield 7.76 g of the product of the example, mp 222°–232° C.

EXAMPLE 7

3′,3″,3‴,5′,5″,5‴-Hexasulfamoyl-1,3,6-naphthalenetrisulfonanilide trisodium salt A solution of 7.0 g of the product of Example 6 plus 880 mg of sodium hydroxide and 1.0 g of sodium acetate trihydrate in 40 ml of water is diluted with 400 ml of absolute ethanol followed by 400 ml of diethyl ether to give a gummy precipitate. The liquid is decanted and saved and the gum is stirred over ethanol:ether (1:1) until solid. The solid is filtered to give 4.1 g of pale yellow powder (A). The decanted liquid above is concentrated to 15 ml and poured into 600 ml of ethanol:ether (1:1) to give a colorless precipitate. The mixture is filtered and the product is washed with ethanol:ether (1:1), then with ether to give 4.1 g of white powder (B). Fractions (A) and (B) are combined and dissolved in 14.0 ml of water, 1.0 g of sodium acetate trihydrate is added and the resulting solution is poured into 600 ml of ethanol:ether (1:1) with vigorous stirring. The mixture is filtered and washed as above, then is dried by conventional means to yield 7.0 g of the product of the example as a pale yellow powder.

EXAMPLE 8
Preparation of Compressed Tablet

| Ingredient | mg/Tablet |
|---|---|
| Active Compound | 0.5–500 |
| Dibasic Calcium Phosphate N.F. | qs |
| Starch USP | 40 |
| Modified Starch | 10 |
| Magnesium Stearate USP | 1–5 |

EXAMPLE 9
Preparation of Compressed Tablet-Sustained Action

| Ingredient | mg/Tablet |
|---|---|
| Active Compound as Aluminum Lake*, Micronized | 0.5–500 (as acid equivalent) |
| Dibasic Calcium Phosphate N.F. | qs |
| Alginic Acid | 20 |
| Starch USP | 35 |
| Magnesium Stearate USP | 1–10 |

*Complement inhibitor plus aluminum sulfate yields aluminum complement inhibitor. Complement inhibitor content in aluminum lake ranges from 5–30%.

EXAMPLE 10
Preparation of Hard Shell Capsule

| Ingredient | mg/Capsule |
|---|---|
| Active Compound | 0.5–500 |
| Lactose, Spray Dried | qs |
| Magnesium Stearate | 1–10 |

EXAMPLE 11
Preparation of Oral Liquid (Syrup)

| Ingredient | % W/V |
|---|---|
| Active Compound | 0.05–5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 12
Preparation of Oral Liquid (Elixir)

| Ingredient | % W/V |
|---|---|
| Active Compound | 0.05–5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 13
Preparation of Oral Suspension (Syrup)

| Ingredient | % W/V |
|---|---|
| Active Compound as Aluminum Lake, Micronized | 0.05–5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 14
Preparation of Injectable Solution

| Ingredient | % W/V |
|---|---|
| Active Compound | 0.05–5 |
| Benzyl Alcohol N.F. | 0.9 |
| Water for Injection | 100.0 |

EXAMPLE 15
Preparation of Injectable Oil

| Ingredient | % W/V |
|---|---|
| Active Compound | 0.05–5 |
| Benzyl Alcohol | 1.5 |
| Sesame Oil qs ad | 100.0 |

EXAMPLE 16
Preparation of Intra-Articular Product

| Ingredient | Amount |
|---|---|
| Active Compound | 2–20 mg |
| NaCl (physiological saline) | 0.9% |
| Benzyl Alcohol | 0.9% |
| Sodium Carboxymethylcellulose | 1–5% |
| pH adjusted to 5.0–7.5 | |
| Water for Injection qs ad | 100% |

EXAMPLE 17
Preparation of Injectable Depo Suspension

| Ingredient | % W/V |
|---|---|
| Active Compound | 0.05–5 (acid equivalent) |
| Polysorbate 80 USP | 0.2 |
| Polyethylene Glycol 4000 USP | 3.0 |
| Sodium Chloride USP | 0.8 |
| Benzyl Alcohol N.F. | 0.9 |
| HCl to Ph 6–8 | qs |
| Water for Injection qs ad | 100.0 |

We claim:
1. The compound 5,5',5"-[1,3,6-naphthalenetris≡-(sulfonylimino)]tris-1,3-benzenedisulfonic acid hexaphenyl ester.
2. The compound 4,4',4"-[1,3,6-naphthalenetriyl-tris≡(sulfonylimino)]tri-benzenesulfonic acid triphenyl ester.